(12) United States Patent
Ausen (10) Patent No.: US 9,358,409 B2
(45) Date of Patent: Jun. 7, 2016

(54) AIR FILTRATION DEVICE

(75) Inventor: David L. Ausen, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 663 days.

(21) Appl. No.: 13/635,936

(22) PCT Filed: Mar. 30, 2011

(86) PCT No.: PCT/US2011/030526
§ 371 (c)(1), (2), (4) Date: Sep. 19, 2012

(87) PCT Pub. No.: WO2011/126887
PCT Pub. Date: Oct. 13, 2011

(65) Prior Publication Data
US 2013/0014752 A1 Jan. 17, 2013

Related U.S. Application Data (60) Provisional application No. 61/321,352, filed on Apr. 6, 2010.

(51) Int. Cl.
*A62B 18/04* (2006.01)
*A61M 16/06* (2006.01)
(Continued)

(52) U.S. Cl.
CPC .......... *A62B 18/045* (2013.01); *A61M 16/0627* (2014.02); *A62B 7/10* (2013.01);
(Continued)

(58) Field of Classification Search
CPC . A61M 16/00; A61M 16/06; A61M 16/0627; A61M 16/105; A62B 7/00; A62B 7/10; A62B 18/00; A62B 18/003; A62B 18/006; A62B 18/02; A62B 18/025; A62B 18/04; A62B 18/045; A62B 18/08; A62B 18/088; A62B 17/00; A62B 17/001; A62B 17/006; A62B 17/04; A62B 19/00; A62B 23/00; A62B 23/02; A42B 3/288
See application file for complete search history.

(56) References Cited

U.S. PATENT DOCUMENTS 4,815,903 A  3/1989  Skidmore, Sr.
5,030,068 A  7/1991  Jacobs
(Continued)

FOREIGN PATENT DOCUMENTS

CN  1548192  7/2005
EP  1571351  9/2005
(Continued)

OTHER PUBLICATIONS

International Search Report for PCT International Application No. PCT/US2011/030526, Mailed Jan. 2, 2012, 3 pages.

*Primary Examiner* — Steven Douglas
*Assistant Examiner* — Colin W Stuart
(74) *Attorney, Agent, or Firm* — Jeffrey M. Olofson (57) ABSTRACT

Air filtering devices may be helmet-mounted or belt-mounted. The air filtering devices include a filtering device shell and a filtering unit. The filtering unit includes a contaminated-air inlet, a filter assembly in fluid communication with the contaminated-air inlet, a blower assembly in fluid communication with the filter assembly via a duct, and containing a filtered-air outlet, and a filtered-air passageway in fluid communication with the blower assembly outlet and leading to breathing headgear. The blower assembly is vibrationally isolated from the filtering device shell by being only attached to the filtering device shell by the duct. The duct includes an elastomeric material.

15 Claims, 5 Drawing Sheets

(51) Int. Cl.
*A62B 18/00* (2006.01)
*A62B 7/10* (2006.01)
*B01D 46/10* (2006.01)
*B01D 46/24* (2006.01)
*B01D 46/42* (2006.01)
*A62B 23/02* (2006.01)
*A62B 19/00* (2006.01)
*B01D 53/04* (2006.01)

(52) U.S. Cl.
CPC .............. *A62B 18/006* (2013.01); *A62B 18/04* (2013.01); *B01D 46/10* (2013.01); *B01D 46/2411* (2013.01); *B01D 46/4236* (2013.01); *A62B 18/003* (2013.01); *A62B 19/00* (2013.01); *A62B 23/02* (2013.01); *B01D 53/0415* (2013.01); *B01D 2258/06* (2013.01); *B01D 2259/4533* (2013.01); *B01D 2259/4541* (2013.01); *B01D 2273/30* (2013.01); *Y10T 29/49002* (2015.01)

(56) References Cited

U.S. PATENT DOCUMENTS

| | | |
|---|---|---|
| 5,283,914 A | 2/1994 | James |
| 6,107,706 A | 8/2000 | Neckermann |
| 6,435,818 B1 | 8/2002 | Gatley, Jr. |
| 6,478,838 B2 | 11/2002 | McSweeney |
| 6,924,980 B2 | 8/2005 | Lehman |
| 7,454,800 B2 | 11/2008 | Taylor |
| 2004/0255364 A1 | 12/2004 | Feher |
| 2006/0196157 A1* | 9/2006 | Greer et al. ............... 55/500 |
| 2006/0213523 A1* | 9/2006 | VanDerWoude et al. ..... 128/863 |
| 2007/0044800 A1 | 3/2007 | Church |
| 2007/0240308 A1 | 10/2007 | Hutchinson |
| 2010/0037891 A1 | 2/2010 | Walker |
| 2010/0140004 A1 | 6/2010 | Ohzono |

FOREIGN PATENT DOCUMENTS

| | | |
|---|---|---|
| JP | S55-85044 U1 | 12/1977 |
| JP | 06-017303 | 1/1994 |

* cited by examiner

AIR FILTRATION DEVICE

CROSS REFERENCE TO RELATED APPLICATIONS

This application is a national stage filing under 35 U.S.C. 371 of PCT/US2011/030526, filed Mar. 30, 2011, which claims priority to U.S. Provisional Patent Application No. 61/321,352, filed Apr. 6, 2010, the disclosure of which is incorporated by reference in its/their entirety herein.

FIELD OF THE DISCLOSURE

The present disclosure pertains to air filtration devices, especially powered air filtration devices.

BACKGROUND

Supplied air respirators are regularly worn in environments where the surrounding air contains or may contain contaminants. Clean air is delivered to the wearer from a supply tank or from a powered air source that drives or draws ambient air through an air filter.

Systems that use a powered air source to supply clean air to the wearer are referred to as powered air purifying respirators, or "PAPRs". PAPRs may come in a variety of types, but two common types are belt pack PAPRs and helmet PAPRs. Belt pack PAPRs typically have two main parts: a facepiece and a filtering unit. The facepiece is worn at least over the nose and mouth of the user (it also may cover the eyes and ears), and the filtering unit is worn about the user's waist. Typically a hose connects the filtering unit to the facepiece. Helmet PAPRs typically include a pivotal visor as a facepiece and a filtering unit contained within or attached to the helmet.

In both types of PAPRs, the filtering unit often includes one or more filter cartridges, a housing, a fan, and an electric motor that drives the fan. The fan and motor are contained within the housing, and the filter cartridges are attached to the housing body. Ambient air is filtered by being drawn through filter elements that are contained within the filter cartridges. The electrically powered fan drives or draws the air through the filter cartridges, through the hose, and into the facepiece interior. Because the fan does the work required for air movement through the PAPR system, the user is able to comfortably receive a clean supply of air with little effort.

Each style of PAPR has advantages and disadvantages. The belt pack style can be easier for a user to wear because the weight of the filtering unit is carried on the waist and not the head. However, having a two piece system can be cumbersome and the connecting hose can interfere with the free movement of the user and also is at risk of becoming tangled, ruptured or even detached. The helmet style PAPR avoids these drawbacks by being a single self-contained unit, but the weight of the filtering unit can be uncomfortable especially when worn for long periods of time.

SUMMARY

The present disclosure is directed to a blower assembly that is isolated from a filtering device shell by being only attached to the filtering device shell by a duct. The duct comprises an elastomeric material.

Also disclosed herein are air filtering devices comprising a filtering device shell and a filtering unit, the filtering unit comprising a contaminated-air inlet, a filter assembly in fluid communication with the contaminated-air inlet, a blower assembly in fluid communication with the filter assembly via a duct, and the blower assembly also containing a filtered-air outlet, and a filtered-air passageway in fluid communication with the blower assembly outlet. The filter assembly comprises a filter member in fluid communication with the contaminated-air inlet, and the blower assembly is vibrationally isolated from the filtering device shell by being only attached to the filtering device shell by the duct. The duct comprises an elastomeric material. The filtered-air outlet is in fluid communication with a breathing head piece. The air filtering device may be helmet-mounted or belt-mounted. In belt-mounted configurations the filtered-air outlet comprises a hose connecting the belt-mounted filtering portion to the breathing head piece portion.

BRIEF DESCRIPTION OF THE DRAWINGS

The disclosure may be more completely understood in consideration of the following detailed description of various embodiments of the disclosure in connection with the accompanying drawings.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present invention. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

The present disclosure provides a powered, portable air filtering device for a powered air purifying respirator or PAPR. The PAPR may be helmet-mounted or belt-mounted. When helmet-mounted, the PAPR is located within the helmet, when belt-mounted the PAPR is located in a belt pack and connected to breathing headgear by a device such as a hose. Air filtering devices are regularly used in environments where the surrounding air contains contaminants or may potentially contain contaminants. Such contaminants include, for example, fumes, gases, particulates, vapors and the like which may be present alone or in combination.

Each style of PAPR has advantages and disadvantages. A common drawback to each, however, is that the motion of the blower can cause vibrations within the filtering device. The vibrations can manifest as physical vibrations as well as sound vibrations. These vibrations can be transmitted to the wearer causing annoyance and discomfort. The PAPRs of the present disclosure are designed to decrease or even eliminate the vibrations caused by the blower by the design and materials choice for the duct connecting the filter assembly to the blower. The duct is designed in such a way that the blower assembly is attached to the helmet only via a duct, with the duct comprising an elastomeric material.

As used herein, the term "powered air purifying respirator or PAPR" means a supplied air respirator that uses a power source to deliver filtered air to breathing headgear.

As used herein, the terms "filtered air" and "filtered-air" means air (or other oxygen-containing gas) that has been filtered. Typically, "filtered-air" is hyphenated when used as an adjective to describe an assembly such as, for example, a "filtered-air chamber" but when used as a noun, "filtered air" is not hyphenated.

As used herein the terms "contaminated air" and "contaminated-air" mean air (or other oxygen-containing gas) that has not filtered and may contain one or more contaminants. Typically, "contaminated-air" is hyphenated when used as an adjective to describe an assembly such as, for example, a "contaminated-air inlet" but when used as a noun, "contaminated air" is not hyphenated.

As used herein, the term "breathing head gear" means an apparatus to which purified air is supplied that is worn by a person, such breathing head gear includes for example facepieces which fit snugly over at least the respiratory passages (nose and mouth) of a person, as well as loose fitting facepieces such as, for example, face shield assemblies hingeably attached to and depending from the front of a helmet.

As used herein, the term "filter bed" means a structure that includes a filter element and that is adapted for connection to or use in a filtering unit, a "curved filter bed" is one that is not planar but has a radius of curvature; generally the curved filter bed is continuous over the length of curvature, i.e. it is not subdivided along the length of curvature into different filter modules; typically the filter bed includes adsorbent particles.

As used herein, the term "filter cartridge" means a structure that includes a filter element and that is adapted for connection to or use in a filtering unit, a "curved filter cartridge" is one that is not planar but has a radius of curvature.

As used herein, the term "filtering unit" means the portion of a PAPR that is responsible for filtering ambient air and causing powered air movement.

As used herein the term "hose" means a device that includes a conduit that has fluid impermeable wall(s) through which air can travel for delivering clean air from a clean air supply source to breathing headgear;

As used herein the term "powered air purifying respirator or PAPR" means a supplied air respirator that uses a power source to deliver filtered air to breathing headgear.

Figure 1A:
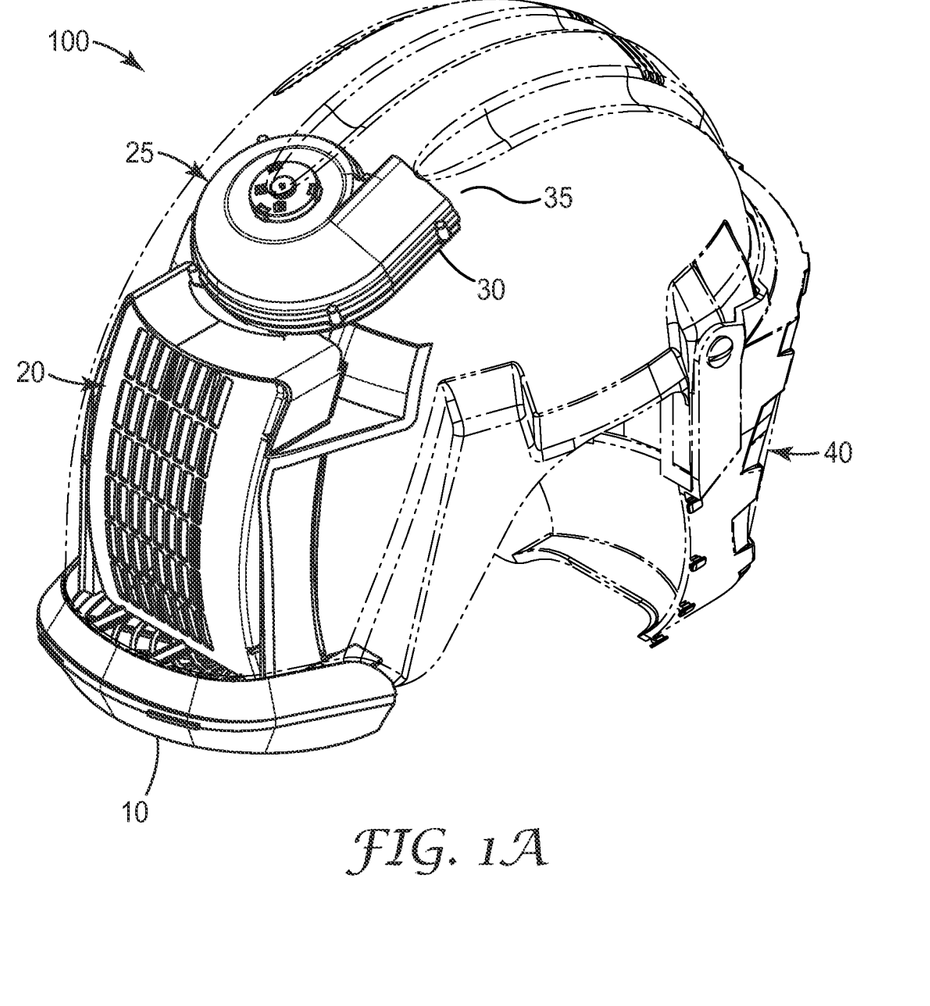
FIG. 1 shows a side view of a helmet-mounted powered air purifying respirator of this disclosure.
Figure 1B:
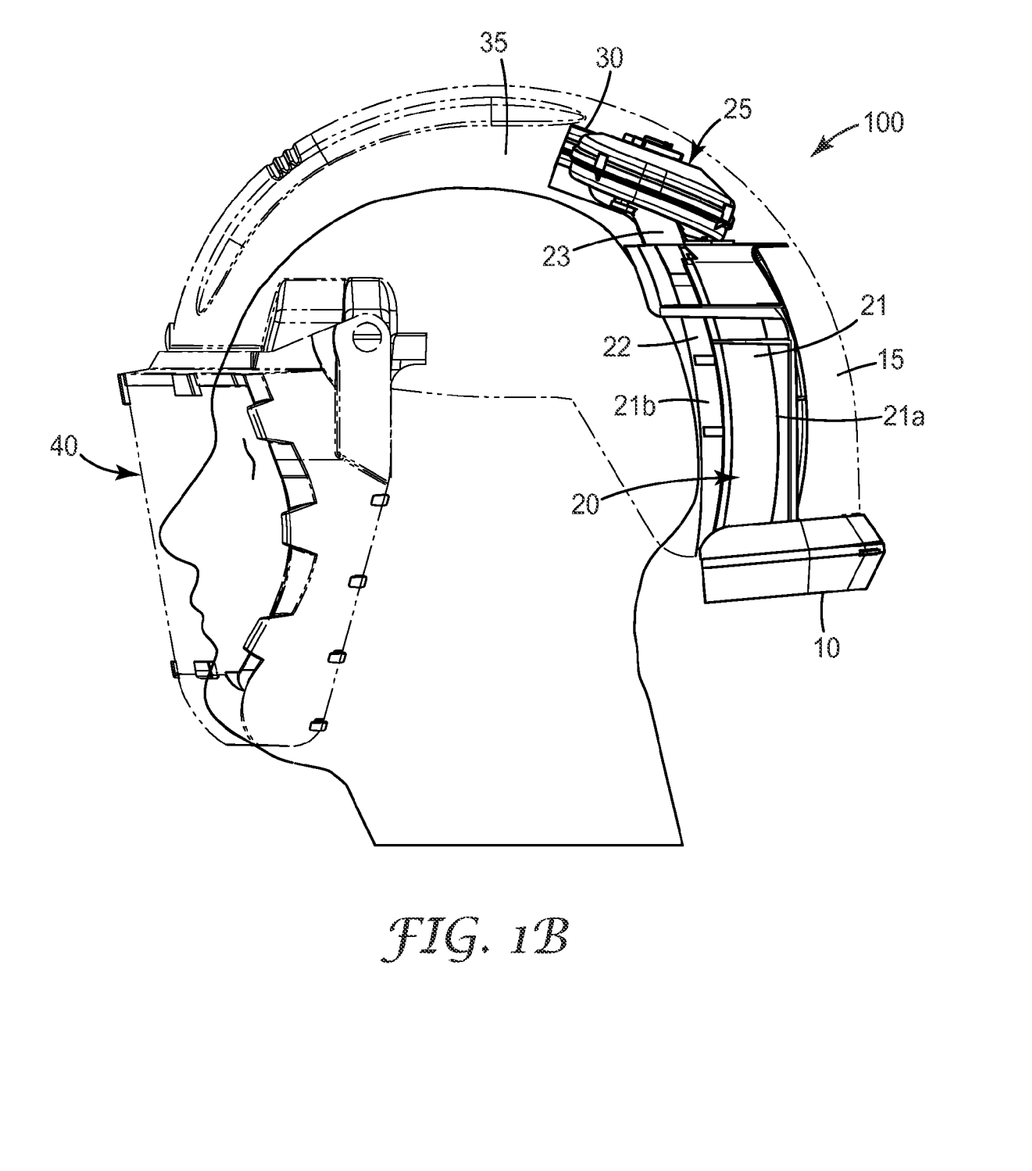

FIGS. 1A and 1B show side views of a helmet mounted PAPR 100. In FIG. 1A, PAPR 100 comprises a motorized system, in which contaminated air enters the PAPR through contaminated air inlet 10, passes through the filter assembly 20, enters blower assembly 25 and exits blower assembly 25 by filtered-air outlet 30. Filtered air outlet 30 is in fluid communication with face shield assembly 40 via channel 35. As shown in further detail in FIG. 1B, contaminated air inlet 10 is in fluid communication with filter assembly 20 via fluid communication passageway 15 which may be a chamber or a channel. Filter assembly 20 comprises filter member 21 which is in fluid communication with blower assembly 25 via fluid communication passageway 22 and duct 23. Duct 23 not only connects blower assembly 25 to fluid communication passageway 22, it also attaches the blower assembly to the filtering device. The contaminated air enters the filter member 21 via filter inlet 21a and filtered-air leaves the filter member 21 via filter outlet 21b. Upon leaving the filter member 21, the filtered air passes through fluid communication passageway 22 and enters blower assembly 25 via duct 23. Upon leaving the blower assembly 25, the filtered-air passes through filtered-air outlet 30.

Contaminated air inlet 10 may be a simple orifice or series of orifices or it may be a more complex apparatus such as, for example, it may contain a pre-filter or screen to reduce the flow of particulates into the PAPR. Examples of pre-filters include, for example, fibrous webs, meshes, foams, non-woven fabrics and the like. The pre-filters may be removable so that they can be removed and cleaned or replaced. Examples of suitable screens include, for example, metal or plastic grids which may be permanently affixed to the inlet or may be removable.

Filter assembly 20 comprises filter member 21. Filter member 21 can include a housing for the filter member, or the filter member may be a stand alone member. Filter member 21 can be constructed from a variety of materials and can target a variety of substances. For example, filter member 21 can include a traditional filter bed, a pleated medium, or any other type of filtering medium or combination of media. The filter medium can include a particulate filtering medium, a chemical filtering medium, or any combination of the two. A chemical filtering medium may include one or more of a sorbent, a catalyst or a chemically reactive medium and may target gases such as ammonia, methylamine, formaldehyde, chlorine, hydrogen chloride, sulfur dioxide, acidic gases, organic vapors or any other desired gas or contaminant. The contaminated air enters the filter member 21 via filter inlet 21a and filtered air leaves the filter member 21 via filter outlet 21b. Filter inlet 21a and filter outlet 21b may simply comprise surfaces of filter member 21, or they may be orifices in the housing for the filter member, if filter member 21 is contained within a housing.

Figure 2:
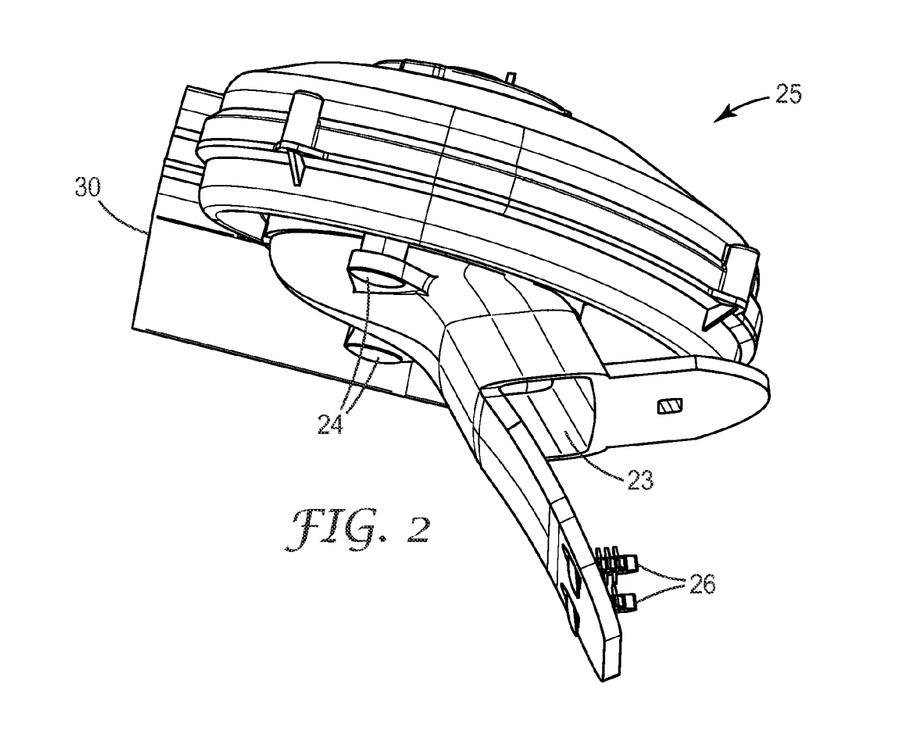
FIG. 2 shows a cut away view of a blower assembly and duct of this disclosure.
Figure 3:
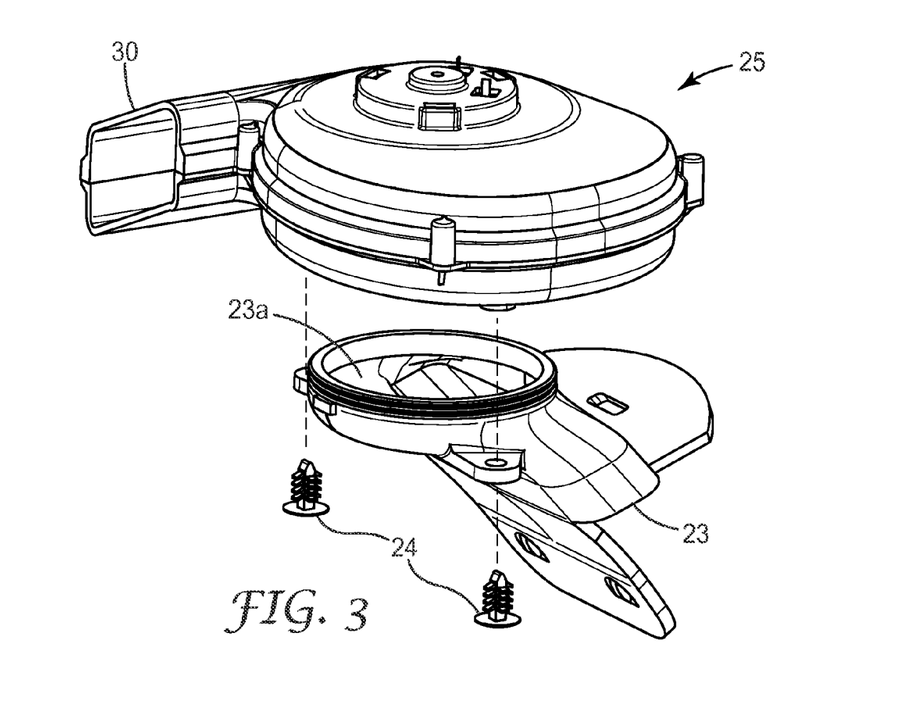
FIG. 3 shows an exploded view of a blower assembly and duct of this disclosure.

Blower assembly 25 and duct 23 that connects blower assembly 25 to the filtering device as well as providing fluid communication for the filtered air to enter the blower assembly, are illustrated in further detail in FIGS. 2 and 3. The inlet of blower assembly 25 (not shown) is attached to duct 23. The blower assembly typically also comprises a blower fan and a motor. The blower motor drives the blower fan which causes the air to flow through the PAPR. Typically, the blower motor is a DC motor. Typically, the power source for the blower motor comprises batteries, either rechargeable or non-rechargeable.

From blower assembly 25, the filtered air passes through filtered-air outlet 30. Filtered-air outlet 30 is in fluid communication with face shield assembly 40. The face shield assembly 40 is adapted to be positioned in the front of the helmet. In some embodiments, the face shield assembly 40 is pivotally attached to and depending from the front of the helmet. Filtered-air outlet 30 may be in fluid communication with a channel, a plurality of channels or it may simply be an orifice leading to the inside portion of the helmet. In FIGS. 1A and 1B, filtered-air outlet 30 leads to a channel 35 (not shown) that is in fluid communication with face shield assembly 40.

As described previously, duct 23 not only connects blower assembly 25 to fluid communication passageway 22, it also is the sole support mechanism for blower assembly 25. Because duct 23 contains or is fashioned from an elastomeric material, any vibrations generated by blower assembly 25 are dampened and not passed along to the filtering device.

A wide range of elastomeric materials may be used to prepare duct 23. For example, thermoplastic elastomers (TPEs), thermoplastic vulcanizates (TPVs), silicones, and natural rubbers, synthetic rubbers or combinations thereof are suitable. The material selection for the duct is generally made to optimize the balance between vibration dampening and structural strength. Materials with a high dampening coefficient are typically very soft and flexible, however, materials suitable for preparing duct 23 also should be rigid enough to support the blower assembly. Specific material properties useful to evaluate potential material candidates may include dampening coefficient, modulus of elasticity, creep rates, and compression set.

FIG. 2 shows a cut away view of blower assembly 25 and duct 23, including filtered-air outlet 30. Filtered air enters blower assembly 25 from duct 23, and exits via filtered-air outlet 30. Duct 23 is in fluid communication with fluid communication passageway 22 (not shown). Duct 23 may be connected to blower assembly 25 by one or more of a variety of different attachment systems, such as mechanical interlocking, pins, screws, snaps, adhesive bonding and the like. In this instance, duct 23 is attached to blower assembly 25 by barbed pins 24. Similarly, duct 23 may be connected to the filtering device by one or more of a variety of different attachment systems, such as mechanical interlocking, pins, screws, snaps, adhesive bonding and the like. In this instance, duct 23 is connected to the filtering device by barbed pins 26.

FIG. 3 shows an exploded view of a blower assembly 25 and duct 23. Duct 23 is attached to blower assembly 25 at duct outlet 23a and attached to blower assembly 25 by barbed pins 24. Duct outlet 23a is configured to attach to and provide a seal with blower assembly 25.

Figure 4:
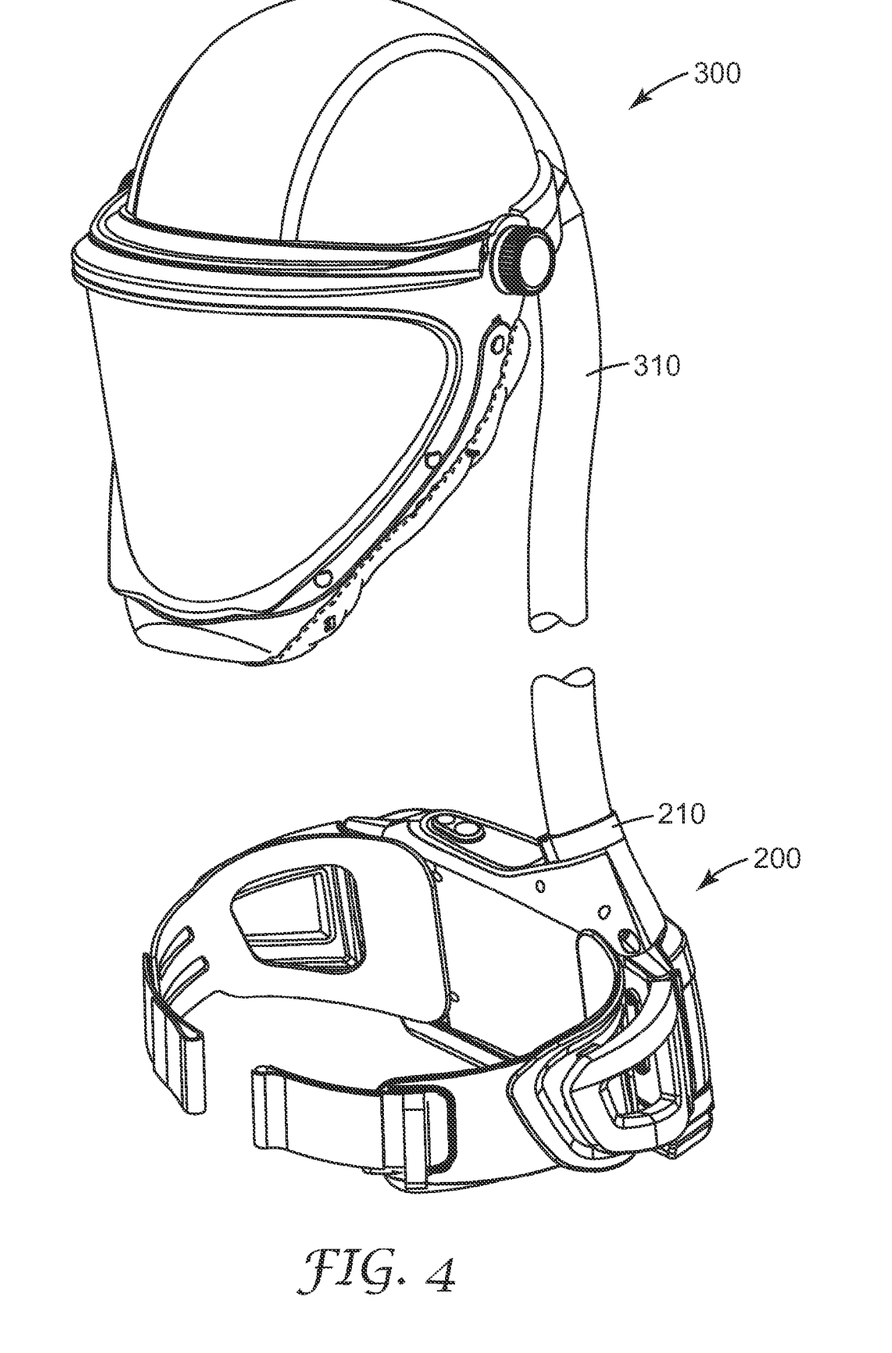
FIG. 4 shows schematically a perspective view of an exemplary embodiment of a powered air purifying respirator of this disclosure.

While a helmet-mounted PAPR 100 is shown in FIG. 1, other types of PAPRs, for example, belt mounted designs, can be used in accordance with the present disclosure. A belt mounted PAPR is shown in FIG. 4. The belt mounted PAPR comprises a belt portion 200 that contains the filter and blower assemblies, and breathing head gear 300 which is attached to the belt portion 200 via hose 310. Hose 310 is attached to filtered-air outlet 210.

Figure 5:
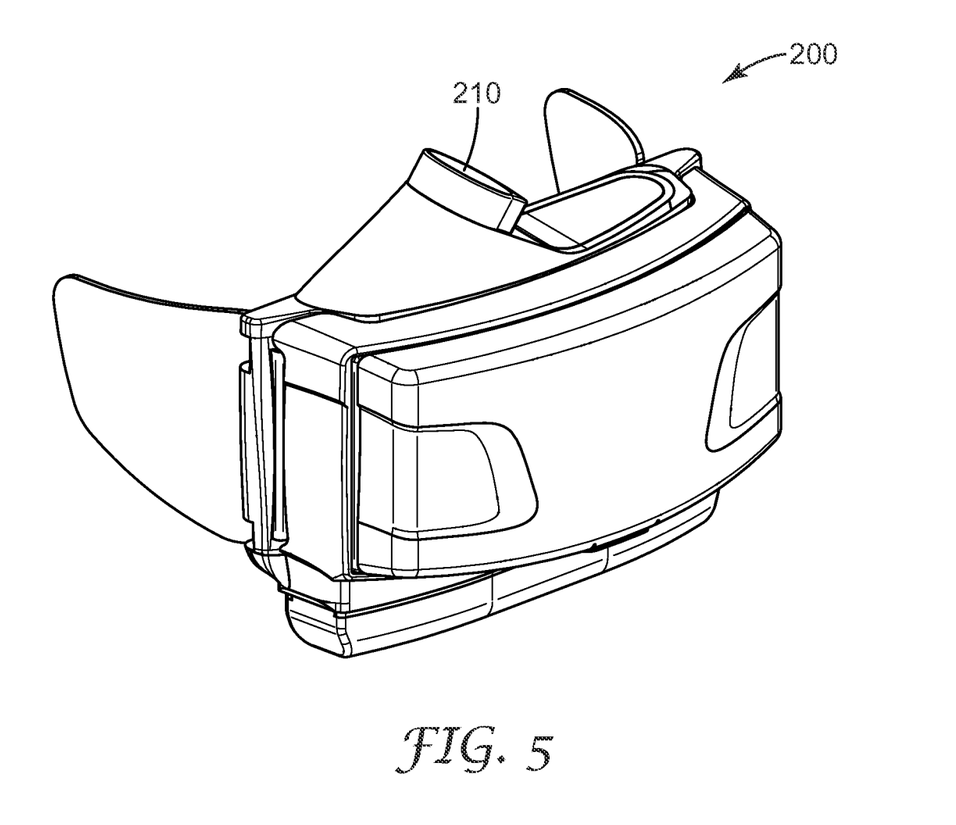
FIG. 5 shows a perspective view of the belt pack filtering unit portion of a powered air purifying respirator of this disclosure.

FIG. 5 shows an expanded view of the belt portion 200 of FIG. 4. The same assemblage of components described for helmet respirator 100 of FIGS. 1A and 1B are present, namely, the contaminated air inlet, filter assembly, blower assembly (not shown) and filtered-air outlet 210. The blower assembly is held in the belt pack by a duct similar to the blower assembly and duct of FIGS. 2 and 3.

What is claimed is:

1. An air filtering device comprising:
    a filtering device shell;
    a blower assembly; and
    a duct formed of a material comprising an elastomeric material, wherein the duct is disposed between the filtering device shell and the blower assembly, wherein the blower assembly is attached to the filtering device shell only by the material of the duct to vibrationally isolate the blower assembly from the filtering device shell, and wherein an inlet of the blower assembly is directly attached to an outlet of the duct.

2. The air filtering device of claim 1, further comprising a filtering unit, the filtering unit comprising:
    a contaminated-air inlet;
    a filter assembly in fluid communication with the blower assembly via the duct, the filter assembly comprising a filter member in fluid communication with the contaminated-air inlet; and
    a filtered-air passageway, wherein the blower assembly further comprises a filtered-air outlet in fluid communication with the filtered-air passageway.

3. The air filtering device of claim 2, wherein the filtering device shell comprises a belt pack and wherein the filtered-air outlet of the blower assembly is in fluid communication with breathing head gear.

4. The air filtering device of claim 2, wherein the filtering device shell comprises a helmet and wherein the filtered-air passageway of the filtering unit is in fluid communication with a face shield assembly adapted to be positioned in a front of the helmet.

5. The air filtering device of claim 2, wherein the filter member comprises a removable filter cartridge.

6. The air filtering device of claim 5, wherein the removable filter cartridge comprises a filter cartridge case and a filter web or a filter bed.

7. The air filtering device of claim 5, wherein the removable filter cartridge comprises a filter web or a filter bed.

8. The air filtering device of claim 1, wherein the filtering device shell comprises a belt pack.

9. The air filtering device of claim 1, wherein the filtering device shell comprises a helmet.

10. The air filtering device of claim 1, wherein the elastomeric material of the duct comprises one or more of a thermoplastic elastomer (TPE), a thermoplastic vulcanizate (TPV), a silicone, a natural rubber, a synthetic rubber, or combinations thereof.

11. The air filtering device of claim 1, wherein the elastomeric material of the duct comprises a vibration damping material.

12. The air filtering device of claim 11, wherein the vibration damping material has a vibration damping property determined by dampening coefficient, modulus of elasticity, creep rate, or compression set.

13. A method of making a powered air respirator comprising:
    attaching a filtering unit within a helmet to form a powered air purifying respirator, the filtering unit comprising:
        a filter assembly;
        a blower assembly comprising a filtered-air outlet;
        a duct formed of a material comprising an elastomeric material disposed between the filter assembly and the blower assembly;
        a contaminated-air inlet, wherein the filter assembly comprises a filter member in fluid communication with the contaminated-air inlet, the filter assembly being in fluid communication with the blower assembly via the duct; and
        a filtered-air passageway in fluid communication with the filtered-air outlet, wherein the blower assembly is vibrationally isolated from the helmet by being attached to the filter assembly only by the material of the duct, and wherein an inlet of the blower assembly is directly attached to an outlet of the duct.

14. A method of making a powered air respirator comprising:
    attaching a breathing head gear to a first end of a hose; and
    attaching a filtering device to the breathing head gear by attaching the filtering device to a second end of the hose to form a powered air purifying respirator, the filtering device comprising:
        a filtering device shell;
        a blower assembly comprising a filtered-air outlet; and
        a duct formed of a material comprising an elastomeric material disposed between the filtering device shell and the blower assembly; and
        a filtering unit, the filtering unit comprising:
            a contaminated-air inlet;
            a filter assembly comprising a filter member in fluid communication with the contaminated-air inlet, the filter assembly being in fluid communication with the blower assembly via the duct; and a filtered-air passageway in fluid communication with the filtered-air outlet, wherein the blower assembly is vibrationally isolated from the filtering device shell by being attached to the filtering device shell only by the material of the duct, wherein an inlet of the blower assembly is directly attached to an outlet of the duct.

15. The method of claim 14, wherein the filtering device shell comprises a belt pack.

* * * * *